United States Patent
Liess et al.

(10) Patent No.: US 12,403,300 B2
(45) Date of Patent: Sep. 2, 2025

(54) ELECTRODE FOR A MEDICAL DEVICE

(71) Applicant: Heraeus Deutschland GmbH & Co. KG, Hanau (DE)

(72) Inventors: Andreas Liess, Hanau (DE); Katharina Musiol, Hanau (DE); Matthias Müller, Hanau (DE); Stefan Rung, Aschaffenburg (DE); Simon Schwarz, Aschaffenburg (DE); Ralf Hellmann, Aschaffenburg (DE)

(73) Assignee: Heraeus Medevio GmbH & Co. KG, Hanau (DE)

( * ) Notice: Subject to any disclaimer, the term of this patent is extended or adjusted under 35 U.S.C. 154(b) by 754 days.

(21) Appl. No.: 17/401,942

(22) Filed: Aug. 13, 2021

(65) Prior Publication Data
US 2022/0054821 A1 Feb. 24, 2022

(30) Foreign Application Priority Data
Aug. 18, 2020 (EP) .................................. 20191600

(51) Int. Cl.
*A61N 1/00* (2006.01)
*A61N 1/05* (2006.01)
*B23K 26/0622* (2014.01)
*B23K 26/359* (2014.01)
*B23K 101/36* (2006.01)
*B23K 103/08* (2006.01)

(52) U.S. Cl.
CPC ............ *A61N 1/05* (2013.01); *B23K 26/0622* (2015.10); *B23K 26/359* (2015.10); *B23K 2101/36* (2018.08); *B23K 2103/08* (2018.08)

(58) Field of Classification Search
None
See application file for complete search history.

(56) References Cited

U.S. PATENT DOCUMENTS

| | | | | |
|---|---|---|---|---|
| 6,229,112 B1* | 5/2001 | Scott | ................... | B23K 26/142 |
| | | | | 219/121.68 |
| 2007/0092637 A1* | 4/2007 | Brown | ................... | B23K 26/40 |
| | | | | 257/E21.252 |
| 2008/0216926 A1* | 9/2008 | Guo | ........................ | C21D 1/09 |
| | | | | 219/121.85 |
| 2016/0059353 A1* | 3/2016 | Dodds | ...................... | A61N 1/05 |
| | | | | 219/121.85 |
| 2019/0283176 A1* | 9/2019 | He | ....................... | B23K 26/122 |

OTHER PUBLICATIONS

Ganske, G., Slavcheva, E., van Ooyen, A., Mokwa, W., & Schnakenberg, U. (2011). Sputtered platinum-iridium layers as electrode material for functional electrostimulation. Thin Solid Films, 519(11), 3965-3970 (Year: 2011).*

* cited by examiner

*Primary Examiner* — John R Downey
*Assistant Examiner* — Anant A Gupta
(74) *Attorney, Agent, or Firm* — Dicke, Billig & Czaja, PLLC

(57) ABSTRACT

One aspect refers to an electrode for a medical device including a monolithic substrate having at least one surface including a continuous pattern, wherein the continuous pattern is formed by at least one set of hollow lines, and wherein the at least one set of hollow lines forms the boundaries of repeating elements. One aspect further relates to a medical device including the electrode according to one embodiment, and to a process for preparing the electrode according to one embodiment.

20 Claims, 6 Drawing Sheets

ELECTRODE FOR A MEDICAL DEVICE

CROSS-REFERENCE TO RELATED APPLICATION

This Utility Patent application claims priority to European Application No. 20 191 600.4 filed on Aug. 18, 2020, which is incorporated herein by reference.

TECHNICAL FIELD

One aspect relates to an electrode for a medical device, to a medical device including the electrode, and to a process for preparing the electrode.

BACKGROUND

Medical devices, and especially active implantable medical devices, contain electrodes to electrically stimulate body tissue such as muscles and nerves.

Electrodes which are implanted in the body of a patient have a specific double layer capacitance. The double layer capacitance is a characteristic of the electrical doubly layer which appears, for examples, at the interface of the electrode to the body tissue and/or body fluids. A high double layer capacitance of the electrode allows for a faster and more efficient dissipation of charges that occur during electrical stimulation. Therefore, an electrode having a high double layer capacitance is usually preferred for medical devices.

It is known that the double layer capacitance of electrodes may be increased by applying so called low impedance coatings such as TiN- or fractal Ir-coatings on the surface of the electrode. These coatings usually have a rough microstructure, which results in a higher double layer capacitance. However, coated electrodes have the disadvantage that the adhesion of the coating to the electrode is always limited. Over time, parts of the coatings can detach from the electrode and can be released to the surrounding of the medical device. This can be highly problematic as detached parts of the coatings can cause inflammation in adjacent body tissue, and therefore can have negative consequences for the health of the patient.

Furthermore, existing technologies of assembling and structuring electrodes and/or medical devices including such electrodes often include many different steps, are highly energy consuming, and/or usually require many different materials or devices, which make the process of preparing of preparing electrodes work intensive and costly.

Thus, it is desirable that an electrode for a medical device, and a process for preparing the same, is provided which does not show the above disadvantages. Specifically, it is desirable that an electrode is provided that has a high double layer capacitance and/or a low impedance, and has a decreased risk of provoking inflammation in body tissue. It is further desirable that the electrode can be prepared by an efficient process. For these and other reasons there is a need for the present embodiment.

One embodiment is directed to the provision of an improved, or at least alternative, electrode for a medical device, and to a process for preparing such an electrode.

SUMMARY

One aspect of one embodiment refers to an electrode for a medical device including a monolithic substrate having at least one surface including a continuous pattern, wherein the continuous pattern is formed by at least one set of hollow lines, and wherein the at least one set of hollow lines forms the boundaries of repeating elements.

The inventors found that the electrode according to one embodiment has an excellent charge storage capacity and very good electrical properties for e.g. a constant current medical device. Furthermore, the electrode is based on a monolithic substrate, which means that no coatings are present on the electrode surface. Therefore, it is excluded that the inventive electrode illustrates a failure of coating adhesion e.g. when used during therapy in the patient's body. In view thereof, possible negative side effects in connection with detached parts of an electrode coating can be avoided.

Another aspect of one embodiment refers to the provision of a medical device which includes the electrode according to one embodiment.

Another aspect of one embodiment relates to a process for preparing the electrode according to one embodiment. The process includes the steps of:
 a) providing an electrode including a monolithic substrate having at least one surface;
 b) continuously laser ablating the at least one surface to obtain a continuous pattern, wherein the continuous laser ablation is carried out using a laser fume and/or laser dust removal system.

The inventors also found that a particularly clean and homogenous continuous pattern can be produced on the surface of the monolithic substrate of the electrode in an energy efficient way by using a laser fume and/or laser dust removal system during a continuous laser ablation of the substrate. This not only allows for preparing a clean electrode with good electrical properties as described herein, but also renders it possible to prepare the specific continuous pattern on the surface of an electrode of an already assembled lead as an essentially final step or as one of the final steps of the production process. This achieves a simple and efficient process of preparing the electrode, and/or the medical device (e.g. lead) including the electrode.

BRIEF DESCRIPTION OF THE DRAWINGS

The following figures illustrate aspects of the embodiments for improving the understanding of the invention in connection with some exemplary illustrations, wherein FIG. 1A illustrates a continuous pattern including two sets of hollow straight lines that cross each other in perpendicular direction (repeating elements: squares). Each set of hollow straight lines has a line pitch of about 20 µm and a line depth ranging between 8 to 14 µm (mean: 11 µm). FIG. 1B illustrates a continuous pattern including two sets of hollow straight lines that cross each other in perpendicular direction (repeating elements: rectangles). The first set of hollow lines in the direction of the x-axis of the pattern has a line pitch of 60 µm, and the second set of hollow lines in the direction of the y-axis of the pattern has a line pitch of 20 µm. The line depth ranges from 10 to 12 µm (mean: 11 µm). FIG. 1C illustrates a continuous pattern including one set of hollow straight lines which extend in the direction of the x-axis of the pattern (repeating elements: straight lines). The set of hollow lines has a line pitch of 20 µm and a line depth ranging from 11 to 14 µm (mean: 12 µm). FIG. 1D illustrates a continuous pattern including one set of hollow waves which extend in the direction of the x-axis of the pattern (repeating elements:

waves). The set of hollow lines has a line pitch of 20 µm and a line depth ranging from 9 to 12 µm (mean: 10 µm).

Figure 2A:
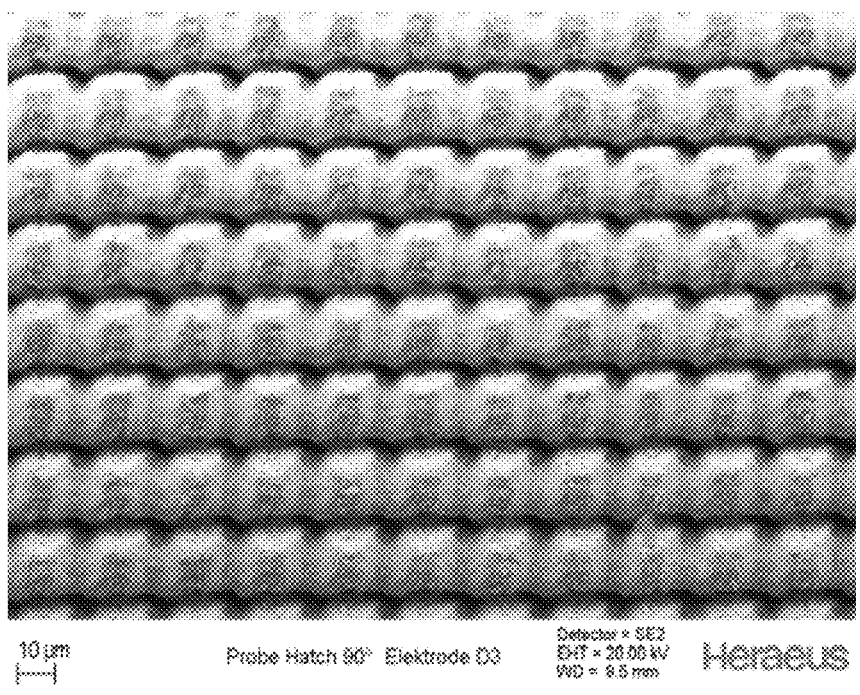
Figure 2B:
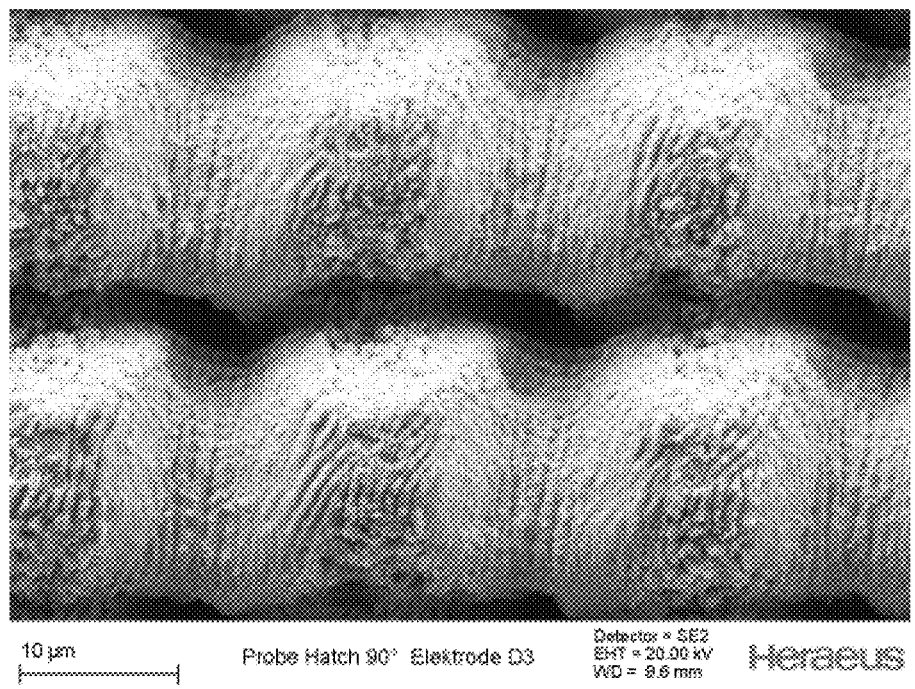
Figure 3A:
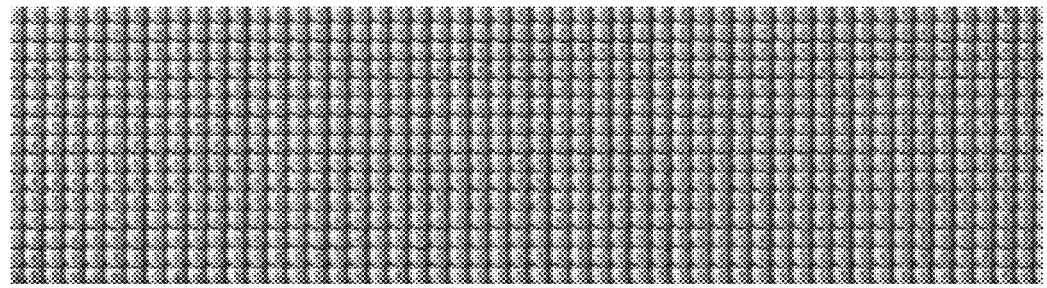
Figure 3B:
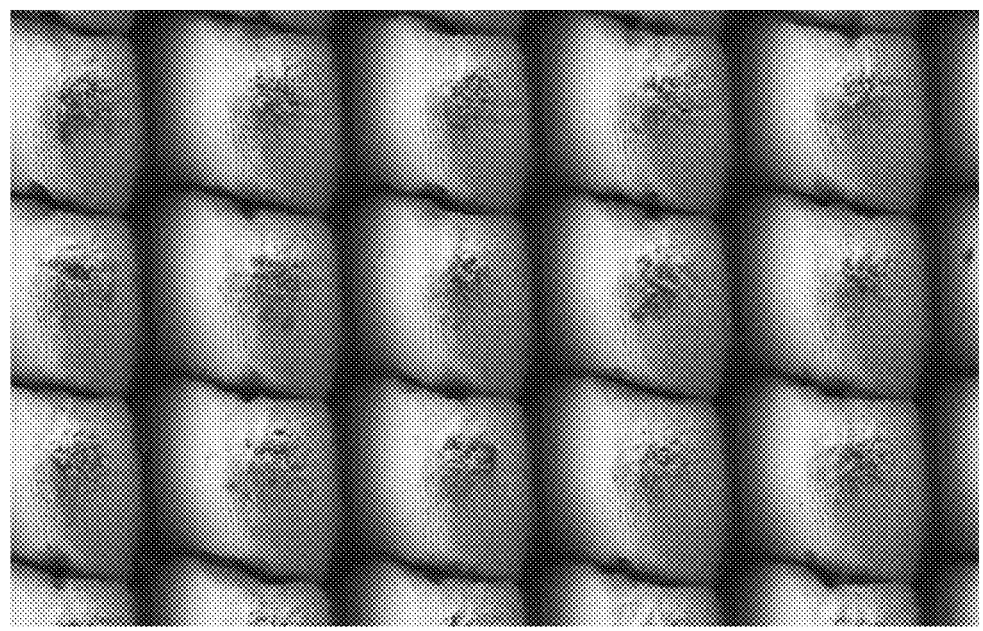
Figure 3C:
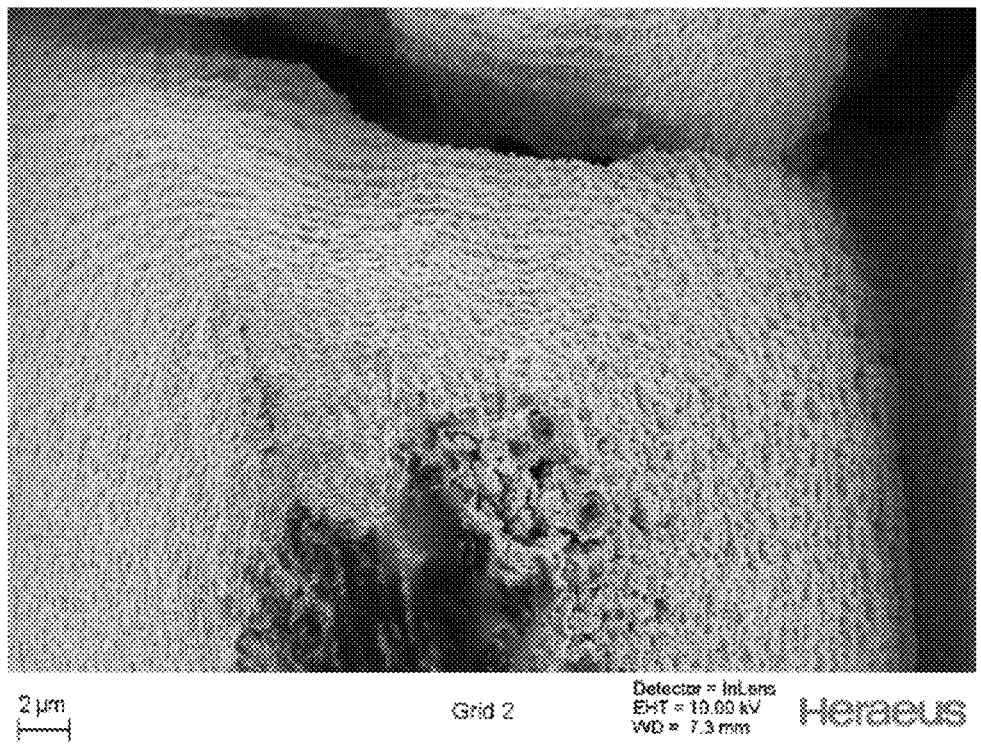
Figure 3D:
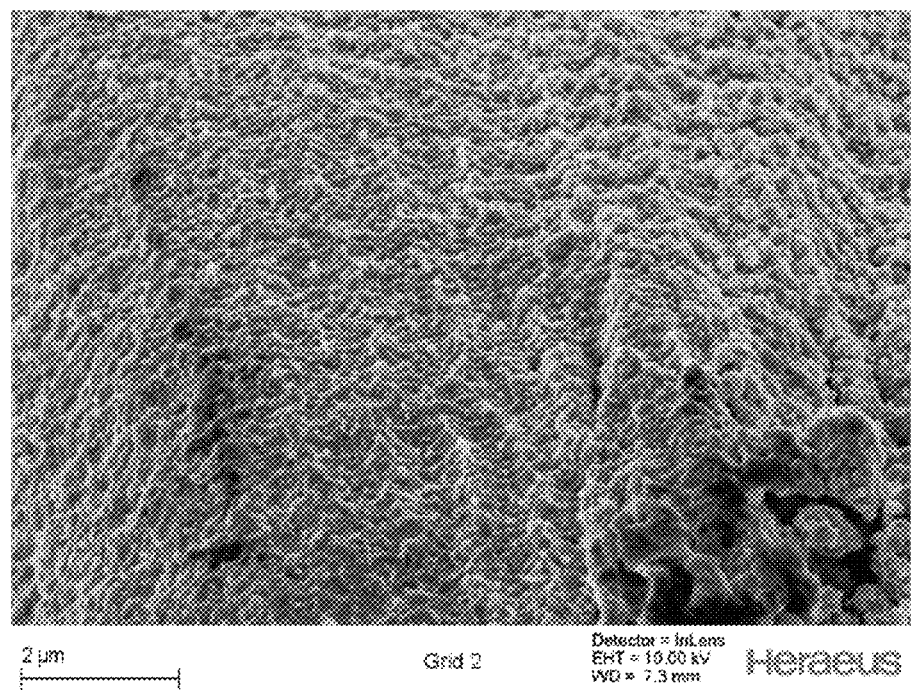
Figure 4A:
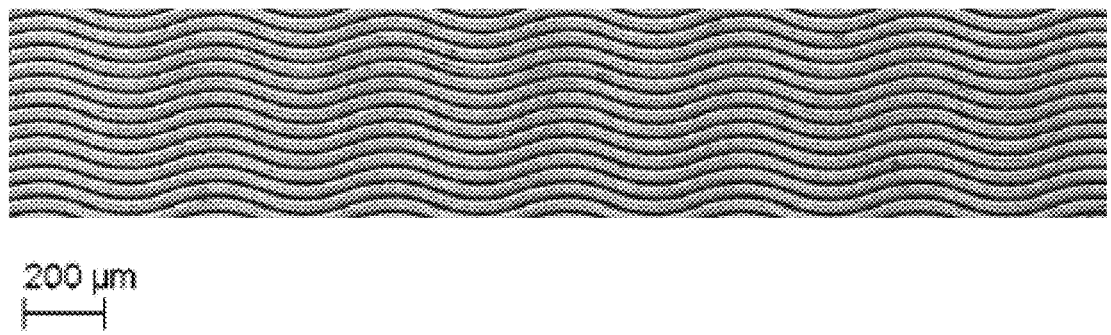
Figure 4B:
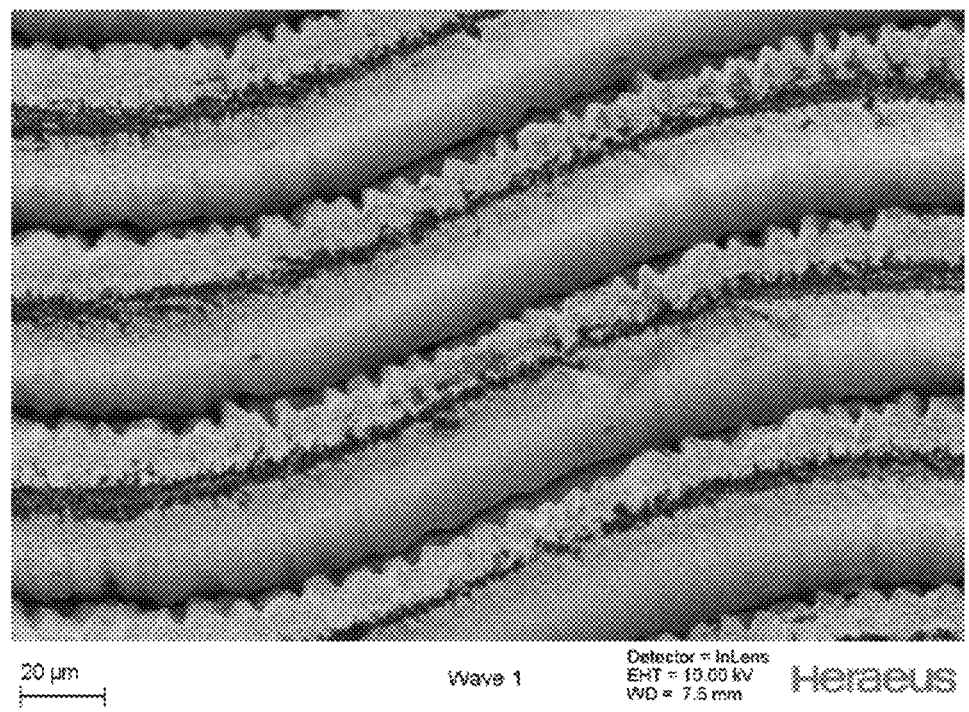
Figure 4C:
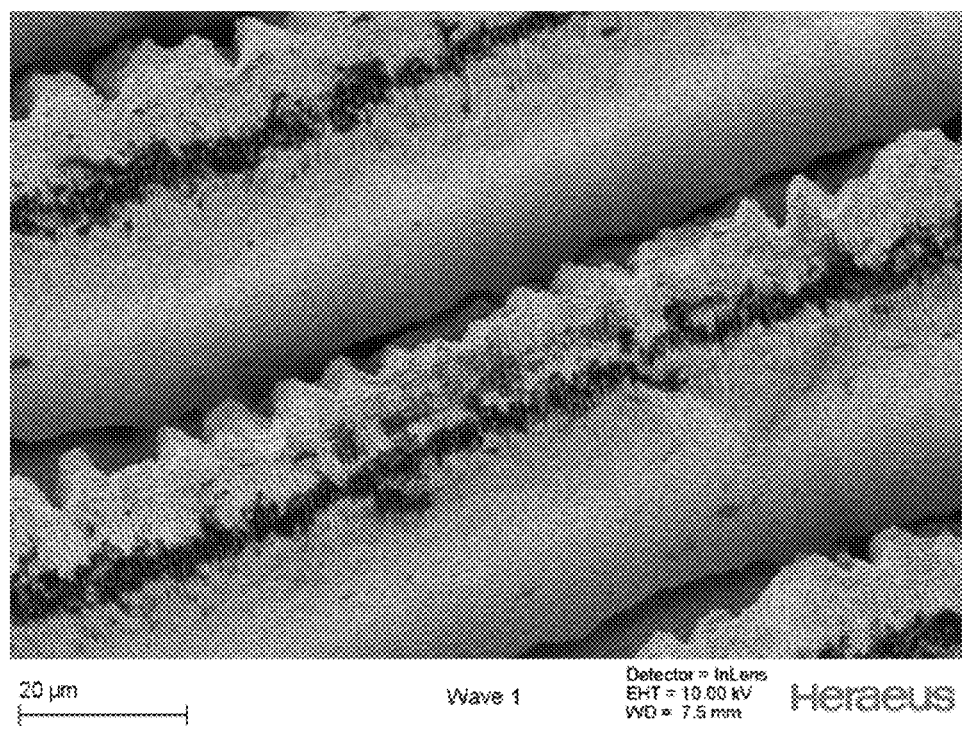
Figure 4D:
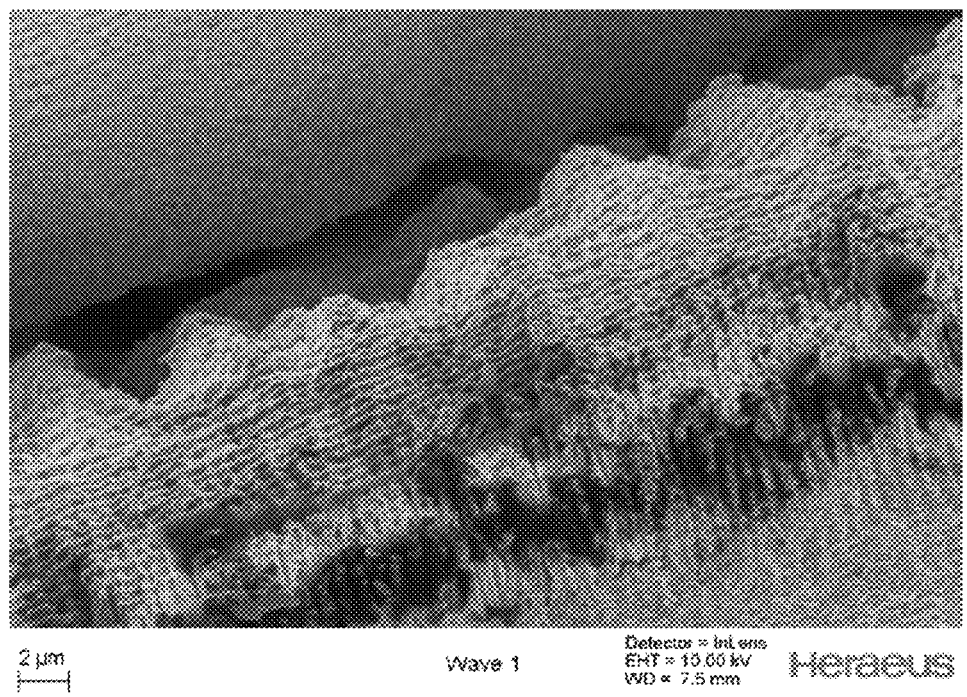

FIGS. 2A and 2B illustrate SEM images of a laser-ablated Pt/Ir alloy ring electrode according to the present embodiment in different order of magnitudes. The laser-ablated platinum ring electrode includes a continuous pattern including two sets of hollow straight lines that cross each other in perpendicular direction (repeating elements: squares). Each set of hollow straight lines has a line pitch of 20 µm and a line depth ranging from 13 to 16 µm (mean: 14 µm) in direction of the x-axis, and 10 to 12 µm (mean: 11 µm) in the direction of the y-axis. In the SEM image illustrated in FIG. 2B, laser-induced periodic surface structures (LIPSS) can be seen on the surface of the substrate in between the repeating elements in form of periodic lines and/or ripples having a width in the range of 0.1 to 2 µm.

FIGS. 3A to 3D illustrate SEM images of a laser-ablated platinum/iridium rectangular electrode according to one embodiment in different order of magnitudes. The laser-ablated platinum/iridium electrode includes a continuous pattern including two sets of hollow straight lines that cross each other in perpendicular direction (repeating elements: squares). Each set of hollow straight lines has a line pitch of 45 µm and a line depth of about 42 µm.

FIGS. 4A to 4D illustrate SEM images of a laser-ablated platinum/iridium rectangular electrode according to one embodiment in different order of magnitudes. The laser-ablated platinum/iridium electrode includes a continuous pattern including one set of hollow waves (repeating elements: waves). The set of hollow waves has a line pitch of 45 µm and a line depth of 45 µm.

DETAILED DESCRIPTION

In the following Detailed Description, reference is made to the accompanying drawings, which form a part hereof, and in which is illustrated by way of illustration specific embodiments in which the embodiment may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present embodiment. The following detailed description, therefore, is not to be taken in a limiting sense, and the scope of the present embodiment is defined by the appended claims.

It is to be understood that the features of the various exemplary embodiments described herein may be combined with each other, unless specifically noted otherwise.

It should be understood that for the purposes of the present embodiments, the following terms have the following meanings:

A "monolithic substrate" in the meaning of the present embodiments is a substrate which is a homogenous material that consists of one chemical compound such as one metal or one metal alloy. A composite material and/or a coated material is not a "monolithic substrate" in the meaning of the patent.

A "continuous pattern" in the meaning of the present embodiments is to be understood as at least one set of hollow lines, which continuously traverses the pattern in one direction of the x-axis and/or the y-axis of the at least one surface.

A "set of hollow lines" is to be understood as referring to at least three lines, which extend, in one embodiment parallel, into the same direction of the at least one surface without crossing each other. It is preferred that the set of hollow lines includes more than three lines (e.g. >10 lines, or >50 lines, or >200 lines, or in the range of 10 to 1 000 000 lines), and the upper limit of lines is only limited by the at least one surface of the monolithic substrate.

The terms "hollow line" and "hollow lines" is to be understood in that a hollow line is a continuous void on the at least one surface of the substrate having a depth of at least 2 µm (e.g. in the range from 2 to 200 µm), a length of at least 100 µm (e.g. in the range from 100 µm to 50 mm), a width of at least 2 µm (e.g. in the range of 2 to 200 µm), and which extends in a direction of an x-axis and/or the direction of a y-axis of the at least one surface. The terms "hollow line" and "hollow lines" as defined herein do not limit the geometrical shape of the line (unless otherwise indicated), and the line or lines can have any shape such as the shape of a straight line, a wave, a curve, a jagged line, and combinations thereof.

"Repeating elements" in the meaning of the present embodiments refers to at least three elements which have essentially the same geometrical shape. It is preferred that the repeating elements includes more than three elements having essentially the same shape (e.g. >20 elements, or >50 elements, or >200 elements, or in the range of 20 to 10 000 000 elements), and the upper limit of repeating elements is only limited by the at least one surface of the monolithic substrate.

"Continuous laser ablation" in the meaning of the present embodiments refers to a laser ablation process having a laser scan path, wherein the start point of the scan path is at least 100 µm (e.g. 100 µm to 50 mm), and in one embodiment at least 250 µm (e.g. 250 µm to 50 mm), away from the end point of the scan path.

Where an indefinite or definite article is used when referring to a singular noun, e.g., "a", "an" or "the", this includes a plural of that noun unless anything else is specifically stated.

Where the term "comprising" is used in the present description and claims, it does not exclude other elements. For the purposes of the present embodiments, the terms "essentially consisting of" and "consisting of" are considered to be a preferred embodiments of the term "comprising". If hereinafter a group is defined to include at least a certain number of embodiments, this is also to be understood to disclose a group, which in one embodiment essentially consists of only of these embodiments, or in one embodiment consists of only of these embodiments.

Terms like "obtainable" or "definable" and "obtained" or "defined" are used interchangeably. This, for example, means that, unless the context clearly dictates otherwise, the term "obtained" does not mean to indicate that, for example, an embodiment must be obtained by, for example, the sequence of steps following the term "obtained" though such a limited understanding is always included by the terms "obtained" or "defined" as a preferred embodiment.

Whenever the terms "including" or "having" are used, these terms are meant to be equivalent to "comprising" as defined hereinabove.

One aspect of one embodiment refers to an electrode for a medical device including a monolithic substrate having at least one surface including a continuous pattern, wherein the continuous pattern is formed by at least one set of hollow lines, and wherein the at least one set of hollow lines form the boundaries of repeating elements.

The electrode includes a monolithic substrate having at least one surface.

The monolithic substrate is in one embodiment a metal or a metal alloy. In one embodiment, the electrode consists of a monolithic metal substrate. In other words, it is preferred that the monolithic metal substrate is the electrode.

It is further preferred that the monolithic metal substrate is a biocompatible metal. The term "biocompatible" in the meaning of the present embodiments is meant to refer to a material which is considered by a person skilled in the art to be safe when being in contact with a living organism (e.g. a human) over a specific period of time (e.g. when used in an implantable medical device). A skilled person knows or can determine whether a metal may be considered biocompatible or not. For example, the biocompatible metal may be a biocompatible metal according to EN ISO 10993.

In one embodiment, the monolithic metal substrate is a metal selected from the group consisting of iron, silver, nickel, palladium, copper, platinum, gold, iridium, steel, titanium, hafnium, niobium, tantalum, cobalt, chromium, zirconium, rhenium, tungsten, molybdenum, and alloys of each one of these metals. According to one embodiment, the monolithic metal substrate is platinum or a platinum alloy (e.g. platinum iridium alloy). In one embodiment, the monolithic metal substrate is a platinum iridium alloy (e.g. Pt/Ir 10). For example, the electrode may be a monolithic platinum substrate or a monolithic platinum/iridium alloy substrate (e.g. Pt/Ir 10).

The monolithic substrate has at least one surface. In general, the shape and/or the dimensions of the monolithic substrate is/are not limited as long as the substrate has at least one surface.

The monolithic substrate may have the shape and/or the dimensions of any known electrode for a medical device. In one embodiment, the monolithic substrate has the shape and/or the dimensions of an electrode of a lead for a medical device. The monolithic substrate may have a cubic, rectangular or cylindrical shape, or a ring shape. The monolithic substrate can be a cubic, rectangular, cylindrical or ring electrode. In one embodiment, the monolithic substrate is a ring electrode.

The monolithic substrate may have a width (or diameter) in the range of 0.1 to 10 mm, and/or a length in the range of 0.1 to 20 mm, and/or a height in the range of 0.1 to 50 mm. In one embodiment, the monolithic substrate has a width (or diameter) in the range of 0.3 to 5 mm, and/or a length in the range of 0.3 to 5 mm, and/or a height in the range of 0.3 to 5 mm. For example, the monolithic substrate may be a ring electrode having a length of 3 mm and a diameter of 1.1 mm.

According to one preferred embodiment, the electrode consists of the monolithic substrate, wherein the monolithic substrate is a metal selected from the group consisting of iron, silver, nickel, palladium, copper, platinum, gold, iridium, steel, titanium, hafnium, niobium, tantalum, cobalt, chromium, zirconium, rhenium, tungsten, molybdenum, and alloys of each one of these metals, in one embodiment a platinum iridium alloy (e.g. Pt/Ir 10), and wherein the electrode has a width (or diameter) in the range of 0.1 to 10 mm, and/or a length in the range of 0.1 to 20 mm, and/or a height in the range of 0.1 to 10 mm.

The monolithic substrate has at least one surface including a continuous pattern. The continuous pattern is not limited to a specific surface of the monolithic substrate. Thus, the monolithic substrate may also have two or more surfaces including a continuous pattern as described herein.

It is also possible that e.g. over 20%, over 50%, over 80% or over 95% of the surface of the monolithic substrate includes the continuous pattern. It is even possible that essentially the whole surface of the monolithic substrate includes the continuous pattern. For example, the monolithic substrate may be an electrode of a lead for a medical device, wherein over 50%, over 80% or essentially the whole surface includes the continuous pattern.

The at least one surface may contain one continuous pattern as described herein, or more than one continuous pattern as described herein. In one embodiment, the at least one surface contains one continuous pattern. In another embodiment, the at least one surface contains two or more continuous pattern (e.g. two continuous pattern or three continuous pattern). Thus, it is to be understood that, for example, an electrode according to one embodiment may include two different continuous pattern as described herein one surface of the monolithic substrate or on two surfaces of the substrate. It is however preferred that the monolithic substrate includes one continuous pattern as described herein.

The continuous pattern may have specific dimensions. For example, the continuous pattern may have a width in the range of 0.1 to 10 mm, in one embodiment from 0.3 to 5 mm, and/or a length in the range of 0.1 to 20 mm, in one embodiment from 0.3 to 5 mm. The "width" of the continuous pattern can be considered as a y-axis of the pattern and the "length" can be considered as an x-axis of the pattern.

The continuous pattern is formed by at least one set of hollow lines, wherein the at least one set hollow lines forms the boundaries of repeating elements.

The hollow lines of the at least one set of hollow lines are not particularly limited in form of geometry and direction in which they extend on and/or traverse the surface, as long as the hollow lines are suitable to create a continuous pattern in the meaning of the present embodiments.

In one embodiment, the hollow lines of the at least one set of hollow lines extend parallel to each other in the same direction. The geometry of the hollow lines of the at least one set of hollow lines are not limited in shape (unless indicated otherwise), and may be waves, straight lines, jagged lines etc.

Figure 1A:
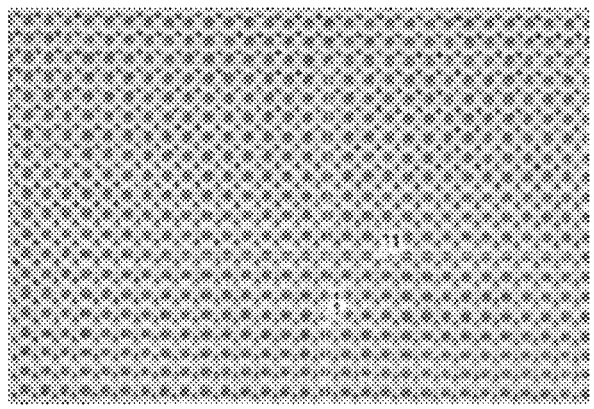
FIGS. 1A to 1D illustrate greyscale images of laser scanning microscopy of exemplary continuous patterns on the surface of several laser-ablated ring electrodes (material: Pt/Ir alloy) on assembled leads.
Figure 1B:
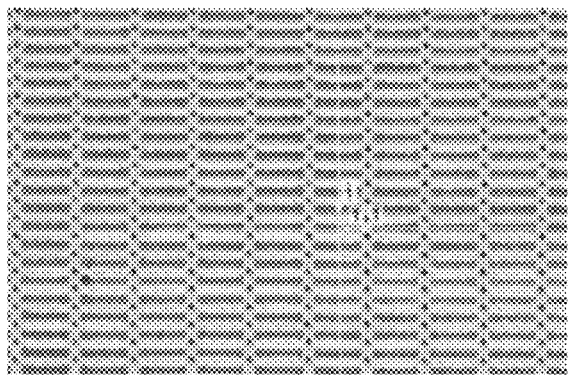
Figure 1C:
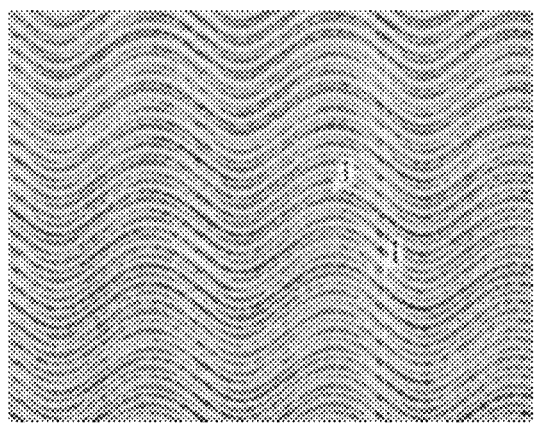
Figure 1D:
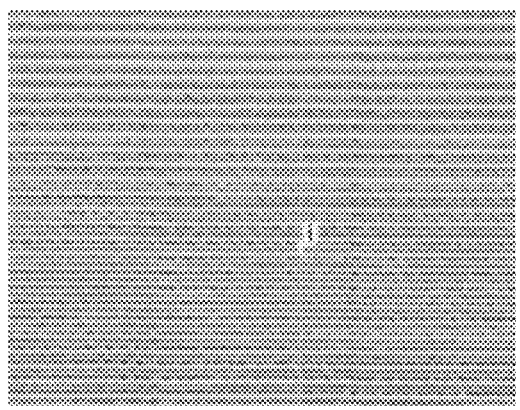

According to one preferred embodiment, the continuous pattern is formed by one set of hollow lines (e.g. straight lines, waves, curves or jagged lines). For example, the continuous pattern may be formed by one set of straight lines or by one set of waves. A continuous pattern with a set of straight lines is illustrated by FIG. 1D and a continuous pattern with a set of waves is illustrated by FIG. 1C. The one set of hollow lines may extend in the direction of a longitudinal axis, a transversal axis, or combination of both, of the monolithic substrate. In one embodiment, the one set of hollow lines extends in the direction of a longitudinal axis or a transversal axis of the monolithic substrate.

It is also possible that the continuous pattern is formed by two or more sets of hollow lines. For example, the continuous pattern may be two or three sets of hollow lines.

According to another preferred embodiment, the continuous pattern is formed by a first set of hollow lines and a second set of hollow lines. The first set of hollow lines and a second set of hollow lines in one embodiment cross each other, e.g. in a perpendicular direction. A continuous pattern with a first set of hollow lines and a second set of hollow lines that cross each other in a perpendicular direction is illustrated by FIGS. 1A and 1B. Continuous pattern as illustrated by FIGS. 1A and 1B may also be referred to as a grid pattern.

Of course, is also possible that the first set of hollow lines and a second set of hollow lines cross each other in a direction, which is not perpendicular (e.g. with an angle of 60° or) 120°. In such a case, a rhombus pattern (or diamond pattern) or a parallelogram pattern may be formed by the two sets of hollow lines.

According to yet another preferred embodiment, the continuous pattern is formed by a first set of hollow lines, a second set of hollow lines and a third set of hollow lines that cross each other (e.g. with an angle of 60° and 120°). In such a case, a triangle pattern may be formed by the three sets of hollow lines.

The at least one set of hollow lines in one embodiment has a specific line pitch. A "line pitch" in the meaning of the present embodiments refers to the distance of one minimum of a hollow line to the another in the set of hollow lines. According to one embodiment, the continuous pattern is formed by at least one set of hollow lines having a line pitch in the range of 1 to 200 µm, in one embodiment 5 to 80 µm, and in one embodiment 10 to 50 µm. In one embodiment, the lines pitch of the at least one set of hollow lines is about 20 µm.

The line pitch, as well as any other dimension in the nano- or micrometer range as described herein, can be determined by the skilled person using scanning electron microscopy (SEM). It is also possible to measure a line pitch, e.g. in the range of 1 to 200 µm, by optical microscopy or confocal optical microscopy (e.g. laser scanning microscopy). One preferred way of determining the line pitch is by laser scanning microscopy.

The inventors found that the electrical performance of the electrode is particularly improved, if the continuous pattern is formed by at least one set of hollow lines having a line pitch which is below 100 µm, and in one embodiment in the range of 10 to 50 µm (e.g. 20 µm).

Given that the hollow lines form the boundary of the repeating elements, a skilled person understands that the line pitch of a continuous pattern being formed by one set of hollow lines specifies one dimension of the repeating elements. For example, if the continuous pattern is formed by one set of hollow lines having a line pitch of 60 µm, the repeating elements have one dimension (e.g. width) which is 60 µm.

The number of set of lines having a specific line pitch may vary depending on which continuous pattern is to be formed on the at least one surface of the substrate. It is possible to have one set of lines, two set of lines, three set of lines etc., wherein each one set of lines has a specific line pitch.

According to one preferred embodiment, the continuous pattern is formed by one set of hollow lines having a line pitch in the range of 1 to 200 µm, in one embodiment 5 to 80 µm, and in one embodiment 10 to 50 µm. In this embodiment, the repeating elements have a width in the range of 1 to 200 µm, in one embodiment 5 to 80 µm, and in one embodiment 10 to 50 µm. The length of the repeating elements is not specifically limited, if the continuous pattern is formed by one set of hollow lines since the lines do not cross. For example, this is the case if the repeating elements are straight lines or waves.

According to another preferred embodiment, the continuous pattern is formed by two or more sets of hollow lines that cross each other, wherein the sets of hollow lines have a line pitch in the range of 1 to 200 µm, in one embodiment 5 to 80 µm, and in one embodiment 10 to 50 µm. Two sets of hollow lines that cross each other means that one set of hollow lines extends in one direction of the pattern (e.g. in the direction of a y-axis), and the other set of hollow lines extends in a different direction (e.g. in the direction of an x-axis) so that the one set of lines crosses the other set of lines.

In one embodiment, the continuous pattern is formed by a first set of hollow lines and a second set of hollow lines, wherein the first set of hollow lines crosses the second set of hollow lines (e.g. in perpendicular direction), wherein the first set of hollow lines and the second set of hollow lines have a line pitch in the range of 1 to 200 µm, in one embodiment 5 to 80 µm, and in one embodiment 10 to 50 µm. In this embodiment, the line pitch of the first set of hollow lines and a second set of hollow lines may be the same or different. If the line pitch is the same, the repeating elements may be squares or rhombuses (depending on the direction and/or angle in which the lines cross). If the line pitch is different, the repeating elements may be rectangles or parallelograms (depending on the direction and/or angle in which the lines cross).

According to one particularly preferred embodiment, the continuous pattern is formed by a first set of hollow lines and a second set of hollow lines, wherein the first set of hollow lines crosses the second set of hollow lines (e.g. in perpendicular direction), and wherein the first set of hollow lines has a line pitch in the range of 5 to 50 µm, in one embodiment 10 to 30 µm, and the second set of hollow lines has a line pitch in the range of 5 to 50 µm, in one embodiment 10 to 30 µm. In one embodiment, the line pitch of the first set of hollow lines and the second set of hollow lines is the same (e.g. about 20 µm).

The inventors found that an electrode having a dense pattern, i.e. a pattern with two or more sets of hollow lines having a rather small line pitch (e.g. grid pattern with 20×20 µm line pitch), results in particularly good electrically properties. On the other hand, the inventors found that an electrode having a less dense pattern (e.g. a rectangle pattern with 20×60 µm line pitch) can have almost comparatively good electrical properties as the denser pattern while requiring less time and energy for preparation of the electrode.

According to another preferred embodiment, the continuous pattern is formed by a first set of hollow lines and a second set of hollow lines, wherein the first set of hollow lines crosses the second set of hollow lines (e.g. in perpendicular direction), and wherein the first set of hollow lines has a line pitch in the range of 5 to 50 µm, in one embodiment 10 to 30 µm, and the second set of hollow lines has a line pitch in the range of 40 to 200 µm, in one embodiment 55 to 120 µm. According to another preferred embodiment, the continuous pattern is formed by at least two sets of hollow lines, wherein a first set of hollow lines has a line pitch in the range of 5 to 50 µm in one embodiment 10 to 30 µm, and a second set of hollow lines has a line pitch in the range of above 50 to 200 µm, in one embodiment 50 to 120 µm, and wherein the first set of hollow lines crosses the second set of hollow lines.

The hollow lines of the at least one set of hollow lines of the continuous pattern have a depth of at least 2 µm. The "depth" of a hollow line is measured from the top level of an adjacent repeating element to the minimum of the hollow line. It is to be understood that where the continuous pattern is formed by two or more sets of hollow lines that cross each other, it may be that the line depth of a hollow line is deeper on the crossing points than the line depth of the lines which do not cross. In other words, the crossing points of the hollow lines may have a line depth which is deeper than the regular line depth of the set of hollow lines. In one embodiment, the line depth of a hollow line is not measured at a crossing point of two hollow lines, but at a position where the hollow lines do not cross.

In one embodiment, the hollow lines of the at least one set of the continuous pattern have a depth in the range of from 2 to 200 µm, in one embodiment in the range of 5 to 100 µm, in one embodiment of 5 to 75 µm, and in one embodiment in the range of 5 to 25 µm.

According to one preferred embodiment, the line depth of the at least one set of hollow lines is in the range of 5 to 30 µm or 8 to 15 µm. According to another preferred embodiment, the line depth of the at least one set of hollow lines is above 30 µm, in one embodiment in the range of above 30 to 100 µm, and in one embodiment 35 to 75 µm.

The at least one set of hollow lines may have a constant or a varying line depth.

According to one preferred embodiment, the continuous pattern is formed by at least one set of hollow lines having a constant line depth. According to one preferred embodiment, the continuous pattern is formed by one set of hollow lines, wherein the lines have a constant line depth. According to one preferred embodiment, the continuous pattern is formed by one set of hollow lines, wherein the lines have a constant line depth in the range of 5 to 75 µm, in one embodiment 5 to 25 µm, in one embodiment 7 to 15 µm.

According to another preferred embodiment, the continuous pattern is formed by two or more, in one embodiment two, sets of hollow lines, wherein a first set of hollow lines has a line depth, which is deeper than the line depth of a second set of hollow lines, and wherein the first set of hollow lines in one embodiment crosses the second set of hollow lines. According to another preferred embodiment, the continuous pattern is formed by two or more sets of hollow lines, wherein a first set of hollow lines has a line depth, which is at least 2 µm deeper (e.g. in the range of 2 to 20 µm) than the line depth of a second set of hollow lines, and wherein the first set of hollow lines in one embodiment crosses the second set of hollow lines.

According to another preferred embodiment, the continuous pattern is formed by two or more, in one embodiment two, sets of hollow lines, wherein a first set of hollow lines has a line depth, which is deeper than the line depth of a second set of hollow lines, and wherein the first set of hollow lines crosses the second set of hollow lines. According to another preferred embodiment, the continuous pattern is formed by two or more sets of hollow lines, wherein a first set of hollow lines has a line depth, which is at least 2 µm deeper (e.g. in the range of 2 to 20 µm) than the line depth of a second set of hollow lines, and wherein the first set of hollow lines crosses the second set of hollow lines.

According to one preferred embodiment, the continuous pattern is formed by one set of hollow lines (e.g. waves or straight lines) having a line pitch in the range of 5 to 150 µm, in one embodiment 5 to 80 µm, in one embodiment 10 to 50 µm, and a line depth in the range of 5 to 75 µm, in one embodiment 5 to 20 µm. According to one preferred embodiment, the continuous pattern is formed by one set of hollow lines (e.g. waves or straight lines) having a line pitch in the range of 5 to 150 µm, in one embodiment 5 to 80 µm, in one embodiment 10 to 50 µm, and a line depth above 30 µm (e.g. 30 to 75 µm).

According to one preferred embodiment, the continuous pattern is formed by two or more, in one embodiment two, sets of hollow lines that cross each other (e.g. in perpendicular direction), wherein a first set of hollow lines has a line pitch in the range of 5 to 50 µm, and a second set of hollow lines has a line pitch in the range of above 50 to 200 µm, in one embodiment above 50 to 120 µm, and a line depth in the range of 5 to 75 µm, in one embodiment 5 to 20 µm. According to one preferred embodiment, the continuous pattern is formed by two or more, in one embodiment two, sets of hollow lines that cross each other (e.g. in perpendicular direction), wherein a first set of hollow lines has a line pitch in the range of 5 to 50 µm, and the second set of hollow lines has a line pitch in the range of above 50 to 200 µm, in one embodiment above 50 to 120 µm, and a line depth above 30 µm (e.g. 30 to 75 µm).

According to another preferred embodiment, the continuous pattern is formed by two or more, in one embodiment two, sets of hollow lines that cross each other (e.g. in perpendicular direction), wherein a first set of hollow lines has a line pitch in the range of 5 to 50 µm, in one embodiment 10 to 30 µm, and a second set of hollow lines has a line pitch in the range of 5 to 50 µm, in one embodiment 10 to 30 µm, and a line depth in the range of 5 to 75 µm, in one embodiment 5 to 20 µm. According to another preferred embodiment, the continuous pattern is formed by two or more, in one embodiment two, sets of hollow lines that cross each other (e.g. in perpendicular direction), wherein the first set of hollow lines has a line pitch in the range of 5 to 50 µm, in one embodiment 10 to 30 µm, and the second set of hollow lines has a line pitch in the range of 5 to 50 µm, in one embodiment 10 to 30 µm, and a line depth above 30 µm (e.g. 30 to 75 µm).

Furthermore, the continuous pattern includes, in one embodiment consists of, hollow lines having a length of at least 100 µm (e.g. 100 µm to 50 mm), in one embodiment of at least 250 µm (e.g. 250 µm to 50 mm). The length of the hollow lines determines the length of the continuous pattern. Thus, the length of the hollow lines may have the same dimension as one dimension of the continuous pattern. According to one embodiment, the continues pattern includes, in one embodiment consists of, hollow lines having a length in the range from 100 µm to 50 mm, in one embodiment 250 µm to 50 mm.

The continuous pattern includes, in one embodiment consists of, hollow lines having a width of at least 2 µm. According to one embodiment, the continuous pattern includes, in one embodiment consists of, hollow lines having a width in the range from 2 to 200 µm, in one embodiment from 2 to 50 µm, in one embodiment from 2 to 30 µm. The "width" of a hollow line is the distance between two repeating elements measured at half height of the repeating element.

According to one preferred embodiment, the continuous pattern includes, in one embodiment consists of, hollow lines having a length in the range from 50 µm to 50 mm, in one embodiment 100 µm to 50 mm, in one embodiment 100 µm to 20 mm, a depth in the range of 5 to 100 µm, in one embodiment 7.5 to 75 µm, and a width of in the range of 2 to 50 µm, and in one embodiment 2 to 30 µm. According to one preferred embodiment, the continuous pattern is formed by at least one set of hollow lines (e.g. one to three sets of hollow lines) having a length in the range from 50 µm to 50 mm, in one embodiment 100 µm to 50 mm, in one embodiment 100 µm to 20 mm, a depth in the range of 5 to 100 µm, in one embodiment 5 to 75 µm, and a width of in the range of 2 to 50 µm, and in one embodiment 2 to 30 µm.

The continuous pattern is formed by at least one set of hollow lines. The at least one set of hollow lines forms the boundaries of repeating elements.

The dimensions of the repeating elements are not specifically limited, as long as the repeating elements are repeating elements in the meaning of the present embodiments.

According to one embodiment, the repeating elements have a width and/or a length in the range of 1 to 200 µm, in one embodiment 5 to 80 µm, and in one embodiment 10 to 80 µm. According to one embodiment, the repeating elements have a width, a length and/or a height in the range of 1 to 200 µm, in one embodiment 5 to 80 µm, and in one embodiment 10 to 80 µm.

The "width" of the repeating element is the one dimension of the repeating element in a horizontal direction of the pattern (e.g. x-axis and/or y-axis), which is smaller or equal to the other dimension of the repeating element in a horizontal direction of the pattern (e.g. x-axis and/or y-axis).

The "length" of the repeating element is the one dimension of the repeating element in a horizontal direction of the pattern (e.g. x-axis and/or y-axis), which is larger or equal to the other dimension of the repeating element in a horizontal direction of the pattern (e.g. x-axis and/or y-axis). In case the "width" of the repeating element is identical to its "length", the terms can be used interchangeably.

The "height" of the repeating element is the dimension of the repeating element in the vertical direction of the pattern.

The "width" of a repeating element is determined by the distance from one minimum of a hollow line being adjacent to the repeating element to the minimum of the next parallel hollow line on the other side of the repeating element.

The "length" of a repeating element is determined by the distance from one minimum of a hollow line being adjacent to the repeating element to the minimum of the next parallel hollow line on the other side of the repeating element. In case of the continuous pattern is formed by only one set of hollow lines, the skilled person understands that the "length" of the repeating element is determined by the length of the continuous pattern.

The "height" of a repeating element is determined by the distance from one minimum of a hollow line being adjacent to the repeating element to the top level of the repeating element.

According to one embodiment, the repeating elements have a width in the range of 1 to 200 µm, in one embodiment 5 to 80 µm, and in one embodiment 10 to 50 µm. According to one embodiment, the repeating elements have a length in the range of 1 to 200 µm, in one embodiment 5 to 80 µm, and in one embodiment 10 to 50 µm. According to one embodiment, the repeating elements have a height in the range of 1 to 200 µm, in one embodiment 5 to 80 µm, and in one embodiment 10 to 50 µm.

According to one preferred embodiment, the repeating elements have a width and a length in the range of 5 to 50 µm, in one embodiment 5 to 30 µm. The width and length of the repeating elements may be the same or different, and in one embodiment is the same.

According to one embodiment, the repeating elements have at least one dimension which is above 50 µm. According to another preferred embodiment, the repeating elements have a width which is below 50 µm (e.g. from 5 to below 50 µm) and a length, which is above 50 µm (e.g. above 50 µm to 50 mm for one set of hollow lines or above 50 µm to 120 µm for two sets of hollow lines that cross each other).

It is to be understood that in case the continuous pattern is formed by one set of hollow lines which form e.g. waves or straight lines as repeating elements, the length of the repeating elements is not specifically limited. For example, the length of the repeating element may then have the length of the continuous pattern.

According to one preferred embodiment, the repeating elements have a width in the range of 1 to 200 µm, in one embodiment 5 to 80 µm, in one embodiment 10 to 50 µm, and in one embodiment in the range of 10 to 30 µm, and a length in the range of 50 µm to 50 mm, and in one embodiment from 100 µm to 5 mm.

According to one preferred embodiment, the repeating elements have a width in the range of 1 to 200 µm, in one embodiment 5 to 80 µm, in one embodiment 10 to 50 µm, and in one embodiment in the range of 10 to 30 µm, a length in the range of 50 µm to 50 mm, in one embodiment from 100 µm to 5 mm, and a height in the range of 1 to 200 µm, in one embodiment 5 to 80 µm, and in one embodiment 10 to 80 µm. According to one preferred embodiment, the repeating elements have a width in the range of 10 to 50 µm, in one embodiment from 10 to 30 µm, a length in the range of 50 µm to 50 mm, in one embodiment from 100 µm to 5 mm, and a height in the range of 5 to 80 µm, and in one embodiment 10 to 80 µm.

However, it is also possible that the length of the repeating elements is limited to a length, which is shorter than the length of the continuous pattern. This is, for example, the case when two or more sets of hollow lines that cross each other form the repeating elements.

According to one embodiment, the repeating elements have a width in the range of 1 to 200 µm, in one embodiment 5 to 80 µm, and in one embodiment 10 to 80 µm, and a length in the range of 1 to 200 µm, in one embodiment 5 to 80 µm, and in one embodiment 10 to 80 µm.

According to one embodiment, the repeating elements have a width in the range of 1 to 200 µm, in one embodiment 5 to 80 µm, and in one embodiment 10 to 80 µm, a length in the range of 1 to 200 µm, in one embodiment 5 to 80 µm, and in one embodiment 10 to 80 µm, and a height in the range of 1 to 200 µm, in one embodiment 5 to 80 µm, and in one embodiment 10 to 80 µm.

According to one preferred embodiments, the repeating elements have a width in the range of 5 to 50 µm, in one embodiment 10 to 30 µm, a length in the range of 5 to 50 µm, in one embodiment 10 to 30 µm. According to one preferred embodiments, the repeating elements have a width in the range of 5 to 50 µm, in one embodiment 10 to 30 µm, a length in the range of 5 to 50 µm, in one embodiment 10 to 30 µm, and a height in the range of 5 to 50 µm, in one embodiment 10 to 30 µm.

According to another preferred embodiments, the repeating elements have a width in the range of 5 to 50 µm, in one embodiment 10 to 30 µm, a length in the range of 10 to 200 µm, in one embodiment above 50 to 100 µm. According to one preferred embodiments, the repeating elements have a width in the range of 10 to 40 µm, in one embodiment 15 to 30 µm, a length in the range of 10 to 200 µm, in one embodiment above 50 to 100 µm, and a height in the range of 5 to 50 µm, in one embodiment 10 to 30 µm.

According to one embodiment, the width of the repeating elements decreases towards their top end. In other words, the repeating elements may taper towards their top.

The repeating elements may have, or may resemble, a specific geometry.

According to one preferred embodiment, the repeating elements of the continuous pattern have a geometry, which is selected from the group of straight lines,
waves,
squares,
rectangles,
grooved rectangles,
rhombuses,
parallelograms, and
triangles.

According to one preferred embodiment, the repeating elements of the continuous pattern have a geometry, which is selected from the group of

- straight lines, in one embodiment having a width in the range of 5 to 200 µm, in one embodiment having a width in the range of 10 to 40 µm,
- waves, in one embodiment having a width in the range of 5 to 200 µm, and in one embodiment having a width in the range of 10 to 40 µm,
- squares, in one embodiment having a width in the range of 5 to 100 µm, in one embodiment 5 to 50 µm, and in one embodiment in the range of 10 to 30 µm,
- rectangles, in one embodiment having a width in the range of 5 to 100 µm and a length in the range of 10 to 200 µm, and in one embodiment having a width in the range of 5 to 50 µm and a length in the range of above 50 to 100 µm,
- grooved rectangles, in one embodiment having a width in the range of 5 to 100 µm and a length in the range of 10 to 200 µm, and in one embodiment having a width in the range of 5 to 50 µm and a length in the range of above 50 to 100 µm,
- rhombuses, in one embodiment having a side length in the range of 5 to 50 µm, and in one embodiment in the range of 10 to 30 µm,
- parallelograms, in one embodiment having a width in the range of 5 to 100 µm and a length in the range of 10 to 200 µm, and in one embodiment having a width in the range of 5 to 50 µm and a length in the range of above 50 to 100 µm,
- triangles, in one embodiment having a side length in the range of 5 to 50 µm, and in one embodiment in the range of 10 to 30 µm.

According to one embodiment, the repeating elements of the continuous pattern are straight lines, in one embodiment having a width in the range of 5 to 200 µm, in one embodiment having a width in the range of 10 to 40 µm.

According to another embodiment, the repeating elements of the continuous pattern are waves, in one embodiment having a width in the range of 5 to 200 µm, and in one embodiment having a width in the range of 10 to 40 µm.

According to another embodiment, the repeating elements of the continuous pattern are squares, in one embodiment having a width in the range of 5 to 50 µm, and in one embodiment in the range of 10 to 30 µm.

According to another embodiment, the repeating elements of the continuous pattern are rectangles, in one embodiment having a width in the range of 5 to 100 µm and a length in the range of 10 to 200 µm, and in one embodiment having a width in the range of 5 to 50 µm and a length in the range of above 50 to 100 µm.

According to yet another embodiment, the repeating elements of the continuous pattern are grooved rectangles, in one embodiment having a width in the range of 5 to 100 µm and a length in the range of 10 to 200 µm, and in one embodiment having a width in the range of 5 to 50 µm and a length in the range of above 50 to 100 µm.

According to yet another embodiment, the repeating elements of the continuous pattern are rhombuses, in one embodiment having a side length in the range of 5 to 50 µm, and in one embodiment in the range of 10 to 30 µm.

According to another embodiment, the repeating elements of the continuous pattern are parallelograms, in one embodiment having a width in the range of 5 to 100 µm and a length in the range of 10 to 200 µm, and in one embodiment having a width in the range of 5 to 50 µm and a length in the range of above 50 to 100 µm.

According to another embodiment, the repeating elements of the continuous pattern are triangles, in one embodiment having a side length in the range of 5 to 50 µm, and in one embodiment in the range of 10 to 30 µm.

The continuous pattern in one embodiment includes a certain surface microstructure. For example, the continuous pattern may include a surface microstructure having at least one dimension in the range of 0.1 to 2 µm.

According to one embodiment of the present embodiment, the continuous pattern includes a laser-induced periodic surface structure (LIPSS). LIPSS are known to the skilled person, and can be determined e.g. by SEM. For example, in the SEM image illustrated in FIG. 2B, LIPSS can be seen on the surface of the substrate in between the repeating elements in form of periodic lines and/or ripples having a width in the range of 0.1 to 2 µm.

In one embodiment, the continuous pattern includes a laser-induced periodic surface structure (LIPSS) having at least one dimension in the range of 0.1 to 2 µm.

In principle, the continuous pattern can be obtained by any known method (e.g. laser structuring method), which is capable of forming the continuous pattern as described herein.

Continuous laser ablation is particularly suitable to form the continuous pattern of the electrode according to one embodiment. Thus, according to one embodiment, the continuous pattern is obtained on the at least one surface by continuous laser ablation.

Furthermore, it is preferred that the continuous pattern is obtained by continuous laser ablation using a laser fume and/or laser dust removal system.

When a surface is laser ablated, particles which have been removed from the substrate by laser ablation can redeposit on the surface. The particles are usually in the nanometer scale, i.e. have a particle size of below 1 micron (e.g. in the range of 5 to below 1000 nm). A continuous pattern as defined herein which is obtained by laser ablation using a laser fume and/or laser dust removal system has particularly little, or essentially no, redeposited particles on its surface. This can be determined by the skilled person e.g. by using SEM.

Thus, in one embodiment, the at least one surface including the continuous pattern includes little redeposited particles having a particle size in the range of below 1000 nm (e.g. in the range of 5 to 1000 nm) on its surface. In another embodiment, the at least one surface including the continuous pattern includes essentially no redeposited particles having a particle size in the range of below 1000 nm (e.g. in the range of 5 to 1000 nm) on its surface. In another embodiment, the at least one surface including the continuous pattern includes at least 10%, in one embodiment at least 20%, in one embodiment at least 50% (e.g. 50 to 99.9%) less redeposited particles having a particle size in the range of below 1000 nm (e.g. in the range of 5 to 1000 nm) on its surface, compared to a surface including the same continuous pattern, but wherein the continuous pattern was not prepared using a laser fume and/or laser dust removal system.

The electrode according to one embodiment is suitable for use in a medical device. In one embodiment, the electrode according to one embodiment is suitable for use in an implantable medical device, and in one embodiment an active implantable medical device (AIMD). Preferred AIMDs are, for example, cardiac pacemakers, cardiac defibrillators, neurostimulators and/or neuromodulators, cochlea implants, implantable cardioverters, nerve, brain, organ or muscle stimulators as well as implantable monitoring devices, hearing aids, retinal implants, muscle stimulators, implantable drug pumps, artificial hearts, bone growth stimulators, prostate implants, stomach implants or the like. In another preferred embodiment, the electrode according to one embodiment is suitable for use in a temporary or short-term used medical device such as a catheter.

It is further preferred that the electrode according to one embodiment is suitable for use in a lead for a medical device.

Another aspect of one embodiment refers to a medical device including the electrode according to one embodiment.

According to one embodiment, the medical device is an implantable medical device, and in one embodiment an active implantable medical device (AIMD). Preferred AIMDs are, for example, cardiac pacemakers, cardiac defibrillators, neurostimulators and/or neuromodulators, cochlea implants, implantable cardioverters, nerve, brain, organ or muscle stimulators as well as implantable monitoring devices, hearing aids, retinal implants, muscle stimulators, implantable drug pumps, artificial hearts, bone growth stimulators, prostate implants, stomach implants or the like. In an exemplary embodiment, the medical device is a neuromodulator.

In another preferred embodiment, the medical device is a temporary or short-term used medical device such as a catheter.

According to one preferred embodiment, the medical device is a lead for an active implantable medical device, an implantable device, a temporary or short-term used medical device, and the like.

Another aspect of one embodiment relates to a process for preparing an electrode according to one embodiment. The process includes the steps of:
  a) providing an electrode including a monolithic substrate having at least one surface;
  b) continuously laser ablating the at least one surface to obtain a continuous pattern, wherein the continuous laser ablation is carried out using a laser fume and/or laser dust removal system.

In step a) of the process according to one embodiment, an electrode including a monolithic substrate having at least one surface is provided.

The type of electrode provided in step a) is not particularly limited as long as the electrode is suitable for use in a medical device. For example, the electrode may be a cubic, rectangular, cylindrical or ring electrode. In one embodiment, the electrode is a ring electrode.

According to one preferred embodiment, the electrode provided in step a) is part of an assembled lead for a medical device. In other words, it is preferred that in step a) of the inventive process, a lead including an electrode is provided, wherein the electrode includes a monolithic substrate having at least one surface.

The assembled lead which may be used in step a) is not particularly limited. According to one embodiment, the assembled lead includes an insulated lead body and an electrode, in one embodiment a ring electrode, as defined herein in connection with step a). In one embodiment, the insulated lead body and the electrode are isodiametric, i.e. have the same outer diameter.

It has been found by the inventors that step b) can be carried out with an electrode being a part of an assembled lead for a medical device. The laser-ablated electrode and the lead being attached to the electrode obtained in step b) illustrate a clean surface, and do not require a grinding of the electrode and/or of the transition from the lead body to the electrode as a post-processing step. Furthermore, the laser-ablated electrode obtained in step b) illustrates good electrical properties. Thus, by providing in step a) an electrode being part of a lead allows for a particular efficient method of preparing the electrode and/or the medical device according to one embodiment.

The electrode provided in step a) includes a monolithic substrate, which is in one embodiment a monolithic metal substrate. In one embodiment, the electrode provided in step a) consists of a monolithic metal substrate.

It is further preferred that the monolithic metal substrate is a biocompatible metal. The term "biocompatible" in the meaning of the present embodiments is meant to refer to a material which is considered by a person skilled in the art to be safe when being in contact with a living organism (e.g. a human) over a specific period of time (e.g. when used in an implantable medical device). A skilled person knows or can determine whether a metal may be considered biocompatible or not. For example, the biocompatible metal may be a biocompatible metal according to EN ISO 10993.

In one embodiment, the monolithic metal substrate is a metal selected from the group consisting of iron, silver, copper, nickel, palladium, platinum, gold, iridium, steel, titanium, hafnium, niobium, tantalum, cobalt, chromium, zirconium, rhenium, tungsten, molybdenum, and alloys of each one of these metals. According to one embodiment, the monolithic metal substrate is platinum or a platinum alloy (e.g. platinum iridium alloy). In one embodiment, the monolithic metal substrate is a platinum iridium alloy (e.g. Pt/Ir 10). For example, the electrode may essentially consist of, or consist of, a monolithic substrate which is a platinum iridium alloy (e.g. Pt/Ir 10).

The monolithic substrate being part of the electrode provided in step a) has at least one surface. In general, the shape and/or the dimensions of the monolithic substrate is/are not limited as long as the substrate has at least one surface. The monolithic substrate may have the shape and/or the dimensions of any known electrode for a medical device. In one embodiment, the monolithic substrate has the shape and/or the dimensions of an electrode of a lead for a medical device. The monolithic substrate may have a cubic, rectangular or cylindrical shape, or a ring shape. The monolithic substrate can be a cubic, rectangular, cylindrical or ring electrode. In one embodiment, the monolithic substrate is a ring electrode.

The monolithic substrate provide in step a) may have a width (or diameter) in the range of 0.1 to 10 mm, and/or a length in the range of 0.1 to 20 mm, and/or a height in the range of 0.1 to 10 mm. In one embodiment, the monolithic substrate has a width (or diameter) in the range of 0.3 to 5 mm, and/or a length in the range of 0.3 to 5 mm, and/or a height in the range of 0.3 to 5 mm. For example, the monolithic substrate may be a ring electrode having a length of 3 mm and a diameter of 1.1 mm.

Step b) of the inventive process refers to continuously laser ablating the at least one surface to obtain a continuous pattern, wherein the continuous laser ablation is carried out using a laser fume and/or laser dust removal system.

Continuous laser ablation relates to a process of removing material from a solid surface, in one embodiment a metal surface, by irradiating the surface with a laser beam. The material of the irradiated surface evaporates, sublimates, and/or is converted to a plasma. The laser ablation step may be carried out using a galvanometer scanner and/or a x-, y-, z- and rotation-axis for the positioning the laser on the surface of the monolithic substrate or the electrode, respectively. Laser ablation and the equipment therefor are known to the skilled person.

It is to be understood that the continuous pattern obtained in step b) is defined by the features, and preferred features, of the continuous pattern being present on the electrode according to one embodiment. All embodiments of the continuous pattern of the inventive electrode as defined above, are also embodiments of the continuous pattern obtained in step b) of the inventive process.

According to one embodiment, the continuous laser ablation in step b) is carried out with a scanning velocity in the range of above 1000 mm/min, in one embodiment in the range of 1200 to 75000 mm/min. For example, the laser ablating can be carried out with a scanning velocity of 1500 mm/min. However, the laser ablation may also be carried out with a much higher velocity, e.g. in the range of 30000 to 75000 mm/min. The spatial pulse overlap may be in the range of 60 to 99.9%.

The inventors found that by continuously laser ablating the surface of the electrode as described herein, an electrode according of one embodiment can be prepared in a particularly time effective manner.

According to one embodiment, the laser ablating in step b) is carried with a laser having wavelength in the range of 250 to 2000 nm, in one embodiment 500 to 1500 nm, and in one embodiment in the range of 800 to 1200 nm, and/or with a laser focal spot diameter in the range of 1 to 200 µm, and in one embodiment 5 to 50 µm. According to one preferred embodiment, the laser ablating in step b) is carried with a laser having wavelength in the range of 250 to 2000 nm, in one embodiment 500 to 1500 nm, and in one embodiment in the range of 800 to 1200 nm, and with a laser focal spot diameter in the range of 1 to 200 µm, and in one embodiment 5 to 50 µm. According to one preferred embodiment, the laser ablating in step b) is carried with a laser having wavelength in the range of 250 to 2000 nm, in one embodiment 500 to 1500 nm, and in one embodiment in the range of 800 to 1200 nm, with a laser focal spot diameter in the range of 1 to 200 µm, and in one embodiment 5 to 50 µm, and a scanning velocity in the range of above 1000 mm/min, in one embodiment in the range of 1200 to 75000 mm/min.

According to one embodiment, the laser ablating step b) is carried out with a pulsed laser, in one embodiment with an ultrashort pulsed laser.

According to one embodiment, the continuous laser ablation in step b) is carried out with a laser pulse repetition rate of 1 kHz to 50 MHz, in one embodiment 20 kHz to 1000 kHz, in one embodiment in the range of 50 to 500 kHz, and in one embodiment in the range of 100 to 200 kHz, and/or a laser pulse duration in the range of 100 fs to 20 ps, in one embodiment 200 fs to 10 ps, and in one embodiment in the range of 500 to 1500 fs, and/or a laser pulse energy in the range of 100 nJ to 5000 µJ, in one embodiment 200 nJ to 1000 µJ, in one embodiment 500 nJ to 100 µJ, and in one embodiment 500 nJ to 20 µJ.

According to one embodiment, the continuous laser ablation in step b) is carried out with a laser pulse repetition rate of 1 kHz to 50 MHz, in one embodiment 20 kHz to 1000 kHz, in one embodiment in the range of 50 to 500 kHz, and in one embodiment in the range of 100 to 200 kHz, and a laser pulse duration in the range of 100 fs to 20 ps, in one embodiment 200 fs to 10 ps, and in one embodiment in the range of 500 to 1500 fs, and a laser pulse energy in the range of 100 nJ to 5000 µJ, in one embodiment 200 nJ to 1000 µJ, in one embodiment 500 nJ to 100 µJ, and in one embodiment 500 nJ to 20 µJ. According to one preferred embodiment, the laser ablating in step b) is carried with a laser pulse repetition rate of 1 kHz to 50 MHz, in one embodiment 20 kHz to 1000 kHz, in one embodiment in the range of 50 to 500 kHz, and in one embodiment in the range of 100 to 200 kHz, and a laser pulse duration in the range of 100 fs to 20 ps, in one embodiment 200 fs to 10 ps, and in one embodiment in the range of 500 to 1500 fs, and a laser pulse energy in the range of 100 nJ to 5000 µJ, in one embodiment 200 nJ to 1000 µJ, in one embodiment 500 nJ to 100 µJ, and in one embodiment 500 nJ to 20 µJ, a laser having wavelength in the range of 250 to 2000 nm, in one embodiment 500 to 1500 nm, and in one embodiment in the range of 800 to 1200 nm, with a laser focal spot diameter in the range of 1 to 200 µm, and in one embodiment 5 to 50 µm, and a scanning velocity in the range of above 1000 mm/min, in one embodiment in the range of 1200 to 75000 mm/min.

A skilled person knows how to adopt the specific parameters for the continuous laser ablation in step b) depending on the desired continuous pattern. For example, a skilled person knows how to adjust the laser pulse energy to the desired laser focal spot.

The continuous laser ablation in step b) is carried out using a laser fume and/or laser dust removal system.

Laser fume and/or laser dust removal systems are also referred to as laser fume and/or laser dust extractors. A laser fume and/or laser dust removal system can remove and eliminate airborne pollutants, dust, and/or fume, which are generated by laser structuring processes such as laser ablation.

The inventors found that by using a laser fume and/or laser dust removal system during the laser ablation step b), a laser-ablated electrode and/or a medical device including such a laser-ablated electrode can be obtained, which has a particularly high surface quality.

The laser fume and/or laser dust removal system may remove the atmosphere with a specific volume flow rate. According to one preferred embodiment, the volume flow rate of the laser fume and/or laser dust removal system is in the range of 150 m$^3$/h to 5000 m$^3$/h, in one embodiment 150 m$^3$/h to 1500 m$^3$/h (e.g. 300 m$^3$/h).

As described above, one of the advantages of the inventive process is that the process can be carried out using the electrode of an assembled lead for a medical device. The laser-ablated electrode obtained in step b) has an excellent surface quality. The electrode and/or the lead including the lead can be used directly after a final cleaning step, and does not need to be ground (e.g. by centerless grinding) in a further process step after step b) to further prepare the surface of the electrode and/or lead. This is particularly advantageous, since a grinding step would destroy, or at least significantly affect, the structure of the continuous pattern on the electrode.

Therefore, according to one embodiment, the process does not contain a step of grinding the laser-ablated electrode obtained in step b).

According to one embodiment, the electrode provided in step a) is part of an assembled lead for a medical device, and the process does not contain a step of grinding the laser-ablated electrode obtained in step b). This does not exclude that the assembled lead and/or the electrode is ground before carrying out step b) of the inventive process (e.g. for adjusting the final outer diameter of the lead).

The features disclosed in the claims, the specification, and the figures may be essential for different embodiments of the claimed invention, both separately and in any combination with each other.

EXAMPLES

Two sets of test trials were carried out:

In test trial 1, the surface of platinum iridium ring electrodes (Pt/Ir 10) of assembled leads was continuously laser-ablated to obtain different electrodes according to one embodiment.

In test trial 2, the surface of a rectangular (sheet-type) platinum/iridium electrodes (Pt/Ir 10) was continuously laser-ablated to obtain different electrodes according to one embodiment.

In both test trials, the obtained electrodes according to one embodiment were compared to an identical electrode, which does not contain the laser-ablated continuous pattern.

The test trials were carried out as follows:

Test Trial 1 (Test No. 2)

An ultrashort pulsed laser specified by a wavelength of 1030 nm, a pulse repetition rate of 200 kHz and a pulse duration of 900 fs was equipped to a micromachining system consisting of a galvanometer scanner as well as x-, y-, z- and rotation-axis for the positioning and structuring of the electrodes. The focal spot of the laser had a diameter of about 20 µm while the process parameters of the laser used for structuring were pulse energies of 1.65 µJ (longitudinal direction) and 1.4 µJ (axial direction). The individual hollow lines were structured by single lines with two scan passes in axial direction and two parallel lines (5 µm distance and single pass) in longitudinal direction. The longitudinal hollow lines were scanned only by the galvanometer scanner while the electrode and/or the lead is rotated stepwise after each hollow line. For the axial direction, the rotation axis was used, while the galvanometer scanner kept its position fixed (only stepping towards the next line after processing). The scanning velocity was 1500 mm/min in both longitudinal and axial direction.

Test Trial 2

An ultrashort pulsed laser specified by a wavelength of 1030 nm, a pulse repetition rate of 200 kHz and a pulse duration of 770 fs was used. The focal spot was 36 µm for a line pitch of 45 µm and 16 µm for a line pitch of 20 µm. The pulse energies were 3 µJ (test no. D) and 10 µJ (test no. B, C, E, F). The scanning velocity was 42000 mm/min for 45 µm line pitch patterns and 69120 mm/min for 20 µm line pitch patterns.

Results of Test Trial 1 (Continuous Laser-Ablation on Platinum Iridium Ring Electrodes of Assembled Leads):

TABLE 1

| Test No. | Continuous pattern (repeating elements) | Dimensions | Impedance Z/Ω (1 Hz)* | Charge storage capacity (mC/cm²)* |
|---|---|---|---|---|
| 1 (comparative) | None | — | 153960 ± 85667 | 0.89 ± 0.42 |
| 2 (inventive) | Squares | Line pitch: 20 × 20 µm; line depth: 8-14 µm (mean: 11 µm) | 1089 ± 43 | 15.87 ± 0.22 |
| 3 (inventive) | Rectangles | Line pitch: 20 × 60 µm; line depth: 10-12 µm (mean: 11 µm) | 1158 ± 31 | 16.18 ± 0.19 |
| 4 (inventive) | Straight lines | Line pitch: 20 µm; line depth: 11-14 µm (mean: 12 µm) | 1593 ± 155 | 12.80 ± 1.13 |
| 5 (inventive) | waves | Line pitch: 20 µm; line depth: 9-12 µm (mean: 10 µm) | 1871 ± 9 | 12.29 ± 0.38 |

*Average values of two test electrodes

As can be gathered from Table 1, the inventive electrodes have significantly improved electrical properties (decreased impedance and increased charge storage capacity) compared to a reference electrode which does not include the continuous pattern of the inventive electrode. Furthermore, it can be seen that a two-dimensional pattern including a first and a second set of hollow lines (e.g. squares) illustrates improved electrical properties compared to a one-dimensional pattern (including one set of hollow lines).

SEM images of the electrode according to test no. 2 are illustrated in FIGS. 2A and 2B.

Results of Test Trial 2 (Laser-Ablation on Sheet-Type Platinum/Iridium Electrodes):

Table 2 illustrates the physical parameters of the electrodes according to Test No. A to F.

TABLE 2

| Test No. | Continuous pattern (repeating elements) | Line pitch (µm) | Line depth (µm) |
|---|---|---|---|
| A (comparative) | — | — | — |
| B (inventive) | Squares | 45 × 45 | 42 |
| C (inventive) | Squares | 45 × 45 | 11 |
| D (inventive) | Squares | 20 × 20 | 12 |
| E (inventive) | Diamonds (0° + 120°) | 45 × 45 | 12 |
| F (inventive) | Triangles (0° + 60° + 120°) | 45 × 45 × 45 | 12 |

Table 3 illustrates the results for cyclic voltammetry (CV) measurements and for electrochemical impedance spectroscopy (EIS) carried out with test electrodes A to F.

TABLE 3

| Test No. | Charge storage capacity (mC/cm²)* | Impedance Z/Ω (1 Hz)* |
|---|---|---|
| A (comparative) | 1.64 ± 0.06 | 174746 ± 12500 |
| B (inventive) | 3.73 ± 0.83 | 21126 ± 3527 |
| C (inventive) | 2.47 ± 0.04 | 38638 ± 1083 |
| D (inventive) | 3.21 ± 0.22 | 24172 ± 467 |
| E (inventive) | 2.14 ± 0.04 | 67319 ± 2571 |
| F (inventive) | 2.39 ± 0.17 | 43773 ± 4177 |

*Average values of three test electrodes

As can be gathered from the results illustrated in Table 3, the charge storage capacity is increased for all inventive electrodes B to F compared to the reference electrode A. The impedance of the inventive electrodes B to F is decreased compared to the reference electrode A as indicated by relative impedance of below 1. The inventive electrodes B and D illustrated the best electrical properties.

Although specific embodiments have been illustrated and described herein, it will be appreciated by those of ordinary skill in the art that a variety of alternate and/or equivalent implementations may be substituted for the specific embodiments illustrated and described without departing from the scope of the present embodiment. This application is intended to cover any adaptations or variations of the specific embodiments discussed herein. Therefore, it is intended that this embodiment be limited only by the claims and the equivalents thereof.

The invention claimed is:

1. A medical device comprising an electrode comprising a monolithic substrate having at least one surface comprising a continuous pattern, wherein the monolithic substrate is a platinum iridium alloy,
   wherein the continuous pattern is formed by at least one set of hollow lines, wherein the hollow lines of the at least one set of hollow lines have a line depth in the range of from 2 to 200 µm; and
   wherein the at least one set of hollow lines forms boundaries of repeating elements, and
   wherein the electrode has a charge storage capacity of at least 2.14±0.04 mC/cm$^2$.

2. The medical device according to claim 1, wherein the platinum iridium alloy is a Pt/Ir 10 alloy.

3. The medical device according to claim 1, wherein the repeating elements have a width and/or a length in the range of 1 to 200 µm, or wherein the repeating elements have a width which is below 50 µm and a length which is above 50 µm.

4. The medical device according to claim 1, wherein the repeating elements have a width and/or a length in the range of 10 to 50 µm.

5. The medical device according to claim 1, wherein the repeating elements have a width and a length in the range of 5 to 50 µm.

6. The medical device according to claim 1, wherein the repeating elements have a width and a length in the range of 10 to 30 µm.

7. The medical device according to claim 1, wherein the continuous pattern is formed by one set of hollow lines having a line pitch in the range of 1 to 200 µm.

8. The medical device according to claim 1, wherein the continuous pattern is formed by one set of hollow lines having a line pitch in the range of 10 to 50 µm.

9. The medical device according to claim 1, wherein the hollow lines of the at least one set of hollow lines have a line depth of above 30 µm.

10. The medical device according to claim 1, wherein the hollow lines of the at least one set of hollow lines have a line depth in the range of from 5 to 25 µm, or wherein the hollow lines of the at least one set of hollow lines have a line depth in the range of 35 to 75 µm.

11. The medical device according to claim 1, wherein the continuous pattern is formed by at least two sets of hollow lines, wherein a first set of hollow lines has a line depth, which is deeper than the line depth of a second set of hollow lines, and wherein the first set of hollow lines crosses the second set of hollow lines.

12. The medical device according to claim 1, wherein the continuous pattern comprises a laser-induced periodic surface structure (LIPSS).

13. The medical device according to claim 1, wherein the continuous pattern comprises a laser-induced periodic surface structure (LIPSS) having a dimension in the range of 0.1 to 2 µm.

14. The medical device according to claim 1, wherein the continuous pattern is obtained on the at least one surface by continuous laser ablation.

15. The medical device according to claim 1, wherein the medical device is selected from a group comprising a lead for an active implantable medical device, an implantable device, and a temporary or short-term used medical device.

16. A process for preparing a medical device according to claim 1, wherein the process comprises:
   a) providing an electrode comprising a monolithic substrate having at least one surface;
   b) continuously laser ablating the at least one surface to obtain a continuous pattern, wherein the continuous laser ablation is carried out using a laser fume and/or laser dust removal system.

17. The medical device according to claim 1, wherein the continuous pattern is formed by at least two sets of hollow lines, wherein a first set of hollow lines has a line pitch in the range of 5 to 50 µm, and a second set of hollow lines has a line pitch in the range of above 50 µm, and wherein the first set of hollow lines crosses the second set of hollow lines.

18. The medical device according to claim 17, wherein the line pitch of the first set of hollow lines is in the range of 10 to 30 µm, and the line pitch of the second set of hollow lines is in the range of 55 to 120 µm.

19. The medical device according to claim 1, wherein the electrode is a ring electrode.

20. The medical device according to claim 19, wherein the ring electrode has a charge storage capacity of at least 12.29±0.38 mC/cm$^2$.

* * * * *